United States Patent [19]
Tull et al.

[11] 3,944,600
[45] Mar. 16, 1976

[54] INDENYLIDENE-3-ACETIC ACID PROCESS FOR PREPARING INDENE ACETIC ACIDS

[75] Inventors: Roger J. Tull, Metuchen; Robert F. Czaja, Scotch Plains; Richard F. Shuman, Westfield; Seemon H. Pines, Murray Hill, all of N.J.

[73] Assignee: Merck & Co., Inc., Rahway, N.J.

[22] Filed: Sept. 30, 1974

[21] Appl. No.: 509,602

Related U.S. Application Data

[63] Continuation-in-part of Ser. No. 426,864, Dec. 20, 1973, Pat. No. 3,870,753, and a continuation-in-part of Ser. No. 486,031, July 5, 1974.

[52] U.S. Cl. ...... 260/515 A; 260/456 P; 260/476 R; 260/488 CD; 260/516; 260/570.8 R; 260/592; 260/607 A; 260/609 D; 260/946; 260/590 C
[51] Int. Cl.² ............... C07C 147/14; C07C 149/00
[58] Field of Search ...................... 260/515 A, 516

[56] References Cited
UNITED STATES PATENTS
3,732,292   5/1973   Hinkley et al. ................. 260/515 A

*Primary Examiner*—James A. Patten
*Attorney, Agent, or Firm*—Mario A. Monaco; Harry E. Westlake, Jr.

[57] ABSTRACT

Process for preparing 5-fluoro-2-methyl-1-(p-methylsulfinylbenzylidene)-indene-3-acetic acid by reacting fluorobenzene with an acid halide, to form an indanone, reaction of the indanone with a methylthio (or methylsulfinyl)benzyl compound to form 5-fluoro-2-methyl-1-(p-methylthiobenzyl) or (p-methylsulfinylbenzyl)-indene and reacting said indene with a glyoxylic acid. The invention also relates to intermediates thereof and processes for said intermediates.

1 Claim, No Drawings

INDENYLIDENE-3-ACETIC ACID PROCESS FOR PREPARING INDENE ACETIC ACIDS

RELATED CASES

This application is a continuation-in-part of U.S. Ser. No. 426,864 filed Dec. 20, 1973, now U.S. Pat. No. 3,870,753, and U.S. Ser. No. 486,031 filed July 5, 1974.

BACKGROUND OF THE INVENTION

The above-mentioned indene-3-acetic acid is a known compound having anti-inflammatory activity as described in U.S. Pat. No. 3,654,349. The compound has been prepared by a number of methods as disclosed in the above-mentioned patent as well as U.S. Pat. No. 3,732,292 issued May 8, 1973 and U.S. application Ser. No. 33,972 filed May 1, 1970, now abandoned. In one of the methods described in U.S. Pat. No. 3,732,292, 5-fluoro-2-methyl-1-(p-methylsulfinylbenzyl)-indene is disclosed as an intermediate. This intermediate is reacted with a glycolic acid ester and the product is subsequently oxidized to the ester of 5-fluoro-2-methyl-1-(p-methylsulfinylbenzyl)-indenylidene-3-acetic acid which is then isomerized and hydrolyzed to achieve the desired compound. Also in U.S. Ser. No. 33,972, the preparation of the indanone intermediate of this invention is described for the preparation of the indene starting material therein. The preparation of said indanone, however, is quite different from the present preparation and involves reacting 3-nitrobenzaldehyde with propionic anhydride to form the appropriate nitrocinnamic acid, reducing said compound to the corresponding amino compound and further reaction to form the α-methyl-3-fluorohydrocinnamic acid. This compound, in turn, is cyclized to form the indanone.

It is an object of this invention to provide new processes for preparing 5-fluoro-2-methyl-1-(p-methylsulfinylbenzylidene)-indene-3-acetic acid. It is a further object to prepare this compound via new processes which are advantageous over the process described above. It is still a further object to prepare the intermediate indanone in a much shorter path, with higher yields than previously described.

DETAILS OF THE INVENTION

In accordance with one aspect of this invention, it has been found that the subject compound can be readily prepared by a combination of reaction steps; namely, by reacting 5-fluoro-2-methyl-1-(p-methylthiobenzyl)-indene with glyoxylic acid, its ester, salt or other derivative which can form the free acid or salt under the reaction conditions of the process to form 5-fluoro-2-methyl-1-(p-methylthiobenzyl)-indenylidene-3-acetic acid, ester or salt which compound is then isomerized and subsequently oxidized to yield the desired product. (Steps 4, 6 and 7 of Flow Sheet I). Alternatively, the indenylidene-3-acetic acid compound may be first oxidized and then isomerized. In another aspect of this invention, 5-fluoro-2-methyl-1-(p-methylsulfinylbenzyl)-indene is reacted with glyoxylic acid, its ester or salt to form directly 5-fluoro-2-methyl-1-(p-methylsulfinylbenzyl)-indenylidene-3-acetic acid, which compound is subsequently isomerized to the desired product. (Steps 4 and 5 of Flow Sheet I). The 5-fluoro-2-methyl-1-(p-methylsulfinyl-(or methylthio)-benzyl)-indenylidene-3-acetic acids are novel compounds and make up another aspect of this invention. These compounds are useful as intermediates for the preparation of 5-fluoro-2-methyl-1-(p-methylsulfinylbenzylidene)-indene-3-acetic acid, as well as final products, as it has been found that they similarly possess anti-inflammatory activity and could be useful for the same purpose as described for the final product of this process.

In still another aspect of this invention, the 5-fluoro-2-methyl-1-(p-methylthiobenzyl or-(p-methylsulfinylbenzyl-))-indene is prepared by reaction of 5-fluoro-2-methyl-1-indanone with a p-methylthiobenzyl or p-methylsulfinyl compound under Grignard or Wittig conditions to form 5-fluoro-2-methyl-1-(p-methylthio-(or p-methylsulfinyl)-benzyl)-indene, which in turn is further reacted as described above. (Steps 3 to 5 or 3, 4, 6, and 7 of Flow Sheet I.)

In a still further aspect of this invention, the 5-fluoro-2-methyl-1-indanone is prepared by reaction of an appropriate ketone under Friedel Crafts conditions to form the desired 5-fluoro-2-methyl-1-indanone which is further reacted as described above. (Steps 2 to 5 or 2 to 4, 6 and 7 of Flow Sheet I.)

Finally in still another aspect of this invention, the ketone is prepared by reaction of fluorobenzene with an appropriate acid halide under Friedel Crafts conditions to form the desired ketone and further reacted as described above. (Steps 1 to 5 or 1 to 4, 6 and 7 of Formula I.) In this step, the Friedel Crafts reaction may be allowed to continue such that the intermediate ketone formed is cyclized in situ to the 5-fluoro-2-methyl indanone.

The invention and its several aspects may be further described by the following Flow Sheet.

FLOW SHEET I

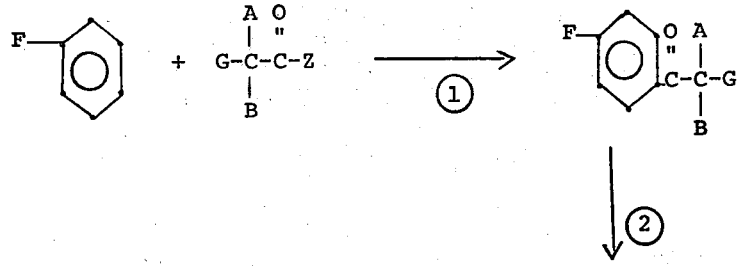

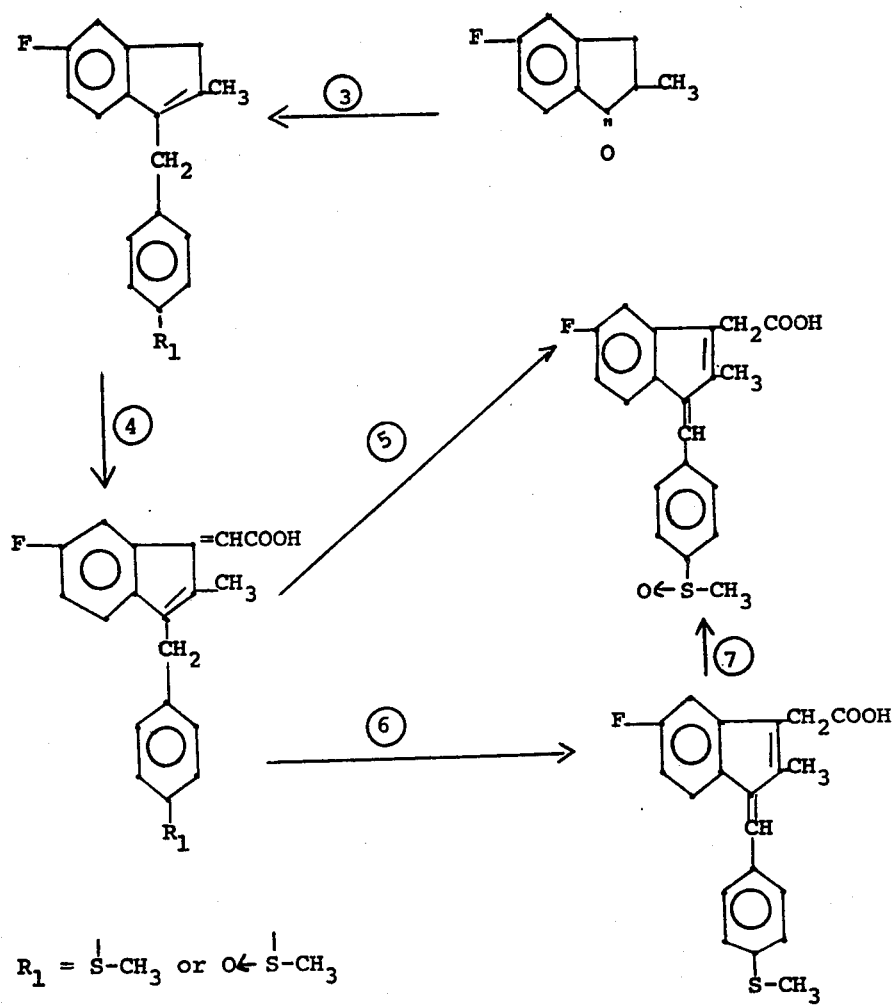

$R_1 = \overset{|}{S}-CH_3$ or $O \leftarrow \overset{|}{S}-CH_3$

More specifically, the condensation reaction between the 5-fluoro-2-methyl-1-(p-methylthio-(or methylsulfinyl-)benzyl)-indene and glyoxylic acid is carried out in the presence of a strong base. Accordingly, bases such as alkali and alkali earth hydroxides (NaOH, KOH) especially in the presence of a quaternary ammonium halide as catalyst (such as $C_{1-6}$ trialkylbenzyl ammonium halide or tetra $C_{1-6}$ alkyl ammonium halide, i.e., 0.1 to 1.0 mole halide to hydroxide), alkali or alkali earth $C_{1-5}$ alkoxide (NaOCH$_3$, K-tertbutoxide), tetra $C_{1-6}$ alkyl ammonium hydroxide or benzyl tri-$C_{1-5}$ alkyl ammonium hydroxides (benzyltrimethyl ammonium hydroxide)-(Triton B)- may be used. Preferably, trialkylbenzyl ammonium hydroxide or tetra-alkyl ammonium hydroxide is used as the strong base. The reaction can be carried out without a solvent, but preferably a solvent is used which is either added to the reaction mixture or employed in conjunction with the strong base. $C_{1-5}$ alkanols (methanol, butanol), aromatic solvents such as benzene, pyridine and toluene or dioxane, acetonitrile, dimethylformamide, triglyme, dimethylsulfoxide, water and mixtures of water and organic solvents may be employed. In fact, any solvent in which the indene and glyoxylic acid are sufficiently soluble can be employed. Preferably, the solvent is $C_{1-5}$ alkanol, especially methanol. The mole ratio of base to glyoxylic acid should be at least slightly more than one mole to one, but preferably about 1.1 to about 4.0 moles of base to glyoxylic acid and especially 1.2 to 2.5. The mole ratio of glyoxylic acid to indene is not critical and may conveniently be from about 1 to 3.0 moles to one and preferably about 1.5 to 1.0 moles of indene. Alternatively, one may use the alkali or alkali earth salt or aryl or alkyl ester, especially $C_{1-5}$ alkyl, i.e., methyl, ethyl, butyl in place of the glyoxylic free acid or any other acid salt of a strong base, as the starting material. Under these circumstances, the amount of strong base employed in the reaction with glyoxylic acid salt or ester need be no more than a catalytic amount, although the ratio indicated above may also be employed. The order of addition of the reactants is not critical; however, it is preferred to add the glyoxylic acid compound to the reaction mixture of indene and base. The time of reaction is not critical, the reaction being carried out until substantial completion. Preferably, however, the reaction is carried out from 15 minutes to about 5 hours and especially from about ½ to 3 hours. The reaction may be carried out from about 0°C to about 150°C, preferably from about 10°C to 80°C and especially from 35°C to 60°C.

After the condensation reaction is complete, the isomerization of the thus formed 5-fluoro-2-methyl-1-(p-methylthio-(or methylsulfinyl)-benzyl)-indenylidene-3-acetic acid, in the form of its acid addition salt or ester, may be carried out without isolation; that is, the same reaction mixture from the glyoxylic acid reaction can be used for the isomerization. This is particularly true when one desires to carry out the isomerization under basic conditions, since the reaction mixture from the previous step is already basic and merely continued reaction will lead to the isomerization product. On the other hand, one may wish to use other strong bases for the isomerization. Such bases as those described for the previous reaction may be employed. Preferably, however, the isomerization is carried out with the use of acid, and accordingly the reaction product from the previous step is preferably first isolated. Various organic and/or inorganic acids may be employed such as $C_{1-5}$ alkylsulfonic acids (methanesulfonic), arylsulfonic acids (toluene sulfonic acid), acidic ion exchange resins (i.e., Dowex 50), arylcarboxylic acids (p-nitrobenzoic acid), aliphatic acids (alkanoic acids such as acetic acid, propionic acid, trichloroacetic acid and trifluoroacetic acid), mineral acids (phosphoric acid, hydrochloric acid, hydrobromic acid and sulfuric acid), but preferably mineral acids or mixtures of mineral acids and organic acids (preferably $C_{2-5}$ alkanoic acids) such as hydrochloric and acetic acid, hydrobromic and propionic acid are employed. The ratio of acid to indenylidene is not critical and one may therefore suitably use catalytic quantities of acid. All that is necessary is that the reaction mixture be made acid in the event that it may be basic. It is preferred, however, to use about 0.1 to 50 moles of acid to indenylidene and especially 1.0 to 20. The reaction may be carried out with our without a solvent, and when solvents are employed those previously mentioned for the glyoxylic acid reaction, which are inert, may be used, as well as halogenated hydrocarbons such as aliphatic halides (ethylene dichloride) or halobenzenes. Preferably, the reaction is carried out with an acid or a halogenated hydrocarbon as solvent. When a weak acid is employed as solvent it is preferred to also employ a strong acid such as the arylsulfonic acids or mineral acids. For example, one could use the unsubstituted alkanoic acids (i.e., acetic acid) as solvent and the arylsulfonic (toluene-sulfonic acid) and especially mineral acids (i.e., hydrochloric acid). When halogenated hydrocarbons are employed as solvents, it is preferred to use mineral acids as catalysts and especially an anhydrous mineral acid such as hydrogen chloride. The time and temperature of reaction is not critical, the higher the temperature the shorter the reaction time needed to substantially complete the reaction. Accordingly, the reaction may be carried out at a temperature of about 0°C to about 150°C and preferably from about 50°C to 110°C. Similarly, the reaction time is preferably at least 30 minutes and may be up to one or more days. After completion of the isomerization reaction, the product may be isolated by standard techniques such as filtration, extraction or removal of the acid solvent by evaporation.

When one uses the p-methylthio compound as the starting material, oxidation of the methylthio group to the desired methylsulfinyl group may be carried out at any stage of the reaction process such as immediately after reaction with glyoxylic acid or after isomerization, but preferably after isomerization. The oxidation may be carried out by any number of standard techniques such as oxidation with $H_2O_2$, basic periodates or hypohalites, preferably the alkaline or alkaline earth periodates and hypohalites or organic peracids such as peracetic acid and monoperphthalic acid. Preferably, however, the oxidizing agent is $H_2O_2$. The reaction is preferably carried out in the presence of a solvent. For such purposes $C_{1-5}$ alkanoic acids (acetic acid), halogenated hydrocarbons (chloroform), ethers (dioxane), $C_{1-5}$ alkanols (isopropanol) or mixtures thereof may be used.

The mole ratio of oxidizing agent to indene compound may be from 0.5 to 10 but preferably from 0.8 to 1.5. The reaction time and temperature are not critical, the reaction being carried out until substantial completion. Preferably, however, the time of reaction is from 1 to 18 hours and especially 2 to 6 hours at a temperature of 10°C to 80°C and especially 25°C to 50°C.

In the event that one desires to use an ester of glyoxylic acid, the final free acid compound is readily obtained during the isomerization especially if some water is present and when the isomerization is carried out at elevated temperatures. The type of ester used is not critical since it can be made to readily come off during the reaction. Accordingly aliphatic, aromatic or heterocyclic esters may be employed such as alkyl (methyl, t-butyl, phenyl, alkenyl) or aryl (benzyl, phenyl). Glyoxylic acid salts may also be used such as the pharmaceutically acceptable salts as well as others which are converted to the free acid by hydrolysis, such salts as alkali or alkali earth (Na, K, Ca, Li) as well as salts of the metals previously described in the Friedel Crafts reaction.

The 5-fluoro-2-methyl-1-(p-methylthio-( or methylsulfinyl)-benzyl)-indene may be prepared from 5-fluoro-2-methyl-1-indanone by reaction with a p-methylthio(or methylsulfinyl)benzyl compound under Grignard or Wittig type conditions. This indene contains the double bond in the 1 to 2 position. However, under certain conditions, in its formation some of the tautomeric indene compounds are present. When these isomers are reacted in the presence of a base as in the reaction with glyoxylic acid, the same indenyl anion is formed which reacts with glyoxylic acid in the same way, giving the indene compound. For example, the Grignard of p-methylthiobenzyl chloride or the Wittig reagent of p-methylsulfinylbenzyl triphenylphosphonium chloride is reacted with 5-fluoro-2-methyl-1-indanone under Grignard or Wittig conditions, respectively. In the case of the Grignard reaction, the benzyl indene compound is obtained directly; whereas with the Wittig reaction, one obtains for the most part the benzylidene indane compound. In this latter case, the benzylidene is isomerized to the benzyl compound under acid conditions by well known means for isomerization.

More specifically, the benzyl group is attached to the indanone compound via a Grignard or Wittig reaction under well known conditions. For example, in the Grignard reaction to metallic magnesium in absolute ether is added the appropriate benzyl halide (Cl, Br, F, I) -(p-methylthiobenzyl halide or p-methylsulfinylbenzyl halide)- and the reaction mixture heated preferably from 25° to 35°C. Although more or less than an equimolar amount of magnesium may be used, it is advantageous to use 3–6 fold excess relative to the benzyl halide. Although diethylether is usually used as the solvent, other ethers may be similarly used such as di-n-butyl, diisopentyl ethers, anisole, cyclic ethers such as tetrahydropyran, 4-methyl-1,3-dioxane, diphydropyran, tetrahydrofurfuryl methyl ether, ethyl ether, furan and 2-ethoxytetrahydrofuran. Tertiary amines such as dimethylaniline, hydrocarbons such as benzene and toluene, as well as many other type solvents described in the literature can be also used. The Grignard reagent thus prepared may be suitably used as is for reaction with the indanone. The indanone and Grignard are admixed (preferably indanone to Grignard) at a temperature of from about 0°C to the boiling point of the solvent and preferably 20 to 35°C. The concentrations of reactants are not critical; however for best results, about equimolar quantities of each are used. The complex thus formed is reacted as is usually done with Grignard reactions with an acid. Inorganic mineral acids such as HCl, $H_2SO_4$ and phosphoric acids may be used as well as organic or aliphatic acids such as acetic, propionic or methanesulfonic. Usually, at least a 5–10% molar excess of acid to complex is used. It is preferred to add the acid to the complex reaction mixture usually as a dilute solution in water, although other solvents for the acid may also be used such as alcohols, ethers or aromatic hydrocarbons. The reaction temperature is usually 0° to 100°C, although 20° to 40°C is preferred.

In the Wittig reaction, for example, triphenylphosphine or a substituted triphenylphosphine is reacted with the appropriate benzyl halide (p-methylthio or p-methylsulfinylbenzyl halide) in the melt or in the presence of suitable solvents to form the intermediate phosphonium salt. Such solvents as (aromatic) benzene, nitrobenzene, xylene (ethers) diethyl ether, acetonitrile or dimethylformamide, (aliphatic) nitromethane, formic acid, acetic acid and ethylacetate as well as many others described in the literature may be used. The preparation of the phosphonium salt is carried out under temperatures well known to the art such as from 0° to 200°C and especially 25° to 75°C, at atmospheric pressure as well as under pressure. The molar concentration of the triphenylphosphine to the benzyl halide may suitably vary from 2 moles to 1 mole and preferably 1.2 moles to 1 mole. The phosphonium salt is not necessarily isolated and is converted to the Wittig reagent employing either the organometallic or alkoxide method. In the former method, phenyl lithium or n-butyl lithium is the usual proton acceptor and diethyl ether or tetrahydrofuran, the solvent. In the latter method an alkali metal alkoxide may be uses as the proton acceptor and corresponding alcohols as the solvent.

The Wittig reagent is usually not isolated but rather is allowed to react in the same reaction vessel. The reaction of the bases with the phosphonium salt is suitably carried out on about an equimolar basis, although an excess of base may be advantageously used. The reaction may be carried out at a temperature of from 0°C to the boiling point of the solvent and preferably from 25° to 50°C. After addition of the base, the indanone compound is then added, suitably about equimolar with the Wittig reagent, although more or less may be used. The reaction may be carried out at temperatures of from 0°C to the boiling point of the solvent but preferably 25° to 50°C until the reaction is substantially complete. The indene intermediate may then be isolated by standard techniques. In those cases wherein the Wittig reagent is first isolated, the reaction with the indanone may be readily carried out in a variety of inert solvents. Solvents such as ether, benzene, ethylacetate, hexane or petroleum ether may be suitably used.

The 5-fluoro-2-methyl-1-indanone is prepared from a ketone of the formula:

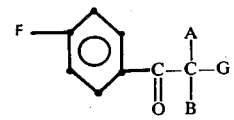

wherein A is methyl or together with G forms methylidene; B is hydrogen, methyl or halo (Cl, Br, F, I); G is methyl, $CH_2R$ or together with A forms methylidene, wherein R is halo (Cl, Br, F, I), hydroxy, its ethers or esters (such as from alkanols -(especially $C_{1-5}$ alkanols), alkanoic acids -(especially $C_{2-5}$ alkanoic acids), aromatic acids -(especially $C_{7-9}$ aromatic acids), mineral acids, i.e., methanol, propanol, acetic acid, propionic acid, methane sulfonic acid, p-toluenesulfonic acid, phosphoric acid, and the like) or $-N-(C_{1-5}$ alkyl$)_2$ especially methyl and ethyl; and when A and G together is methylidene, B is methyl; when A and G are each methyl, B is halo; and when A is methyl and B is hydrogen, G is $CH_2R$; is reacted under Friedel Crafts conditions to form 5-fluoro-2-methyl-1-indanone. Preferably, the ketone starting material is 2-bromo-4'-fluoro-2-methylpropionphenone (when A and G are each methyl and B is halogen) but may suitably also be 4'-fluoro-2-methylacrylophenone, 3-chloro-4'-fluoro-2-methylpropionphenone, 4'-fluoro-3-hydroxy-2-methylpropiophenone or 3-dimethylamino-4'-fluoro-2-methylpropiophenone. The reaction is suitably carried out under normal Friedel Crafts conditions. For example, the ketone is reacted in the presence of such Friedel Crafts catalysts as Lewis acids, metal alkyls and alkoxides, Bronsted acids, acidic oxides and sulfides, cation exchange resins, metathetic cation forming agents and stable carbonium and related complexes. Lewis acids such as those of the acid halide type (metal halides), i.e., aluminum chloride or bromide, $BeCl_2$, $CdCl_2$, $ZnCl_2$, $BF_3$, $BCl_3$, $BBr_3$, $GaCl_3$, $GaBr_3$, $TiCl_4$, $TiBr_4$, $ZrCl_4$, $SnCl_4$, $SnBr_4$, $SbCl_5$, $SbCl_3$, $BiCl_3$, $FeCl_3$ and $UCl_4$ may be suitably used. Also, when the ketone is the α or β-haloisobutyrophenone, the metals per se may be used as catalysts, since in the course of the reaction the halo compound reacts with the metal forming the corresponding metal halide, which in turn assists in furthering the reaction. This class of Friedel Crafts catalysts is preferred and particularly the use of an aluminum or iron halide. The metal alkyl and alkoxides which can be suitably used are, for example, aluminum or boron alkyls (methyl, ethyl, propyl) or alkoxides (methoxide, ethoxide or propoxide). Bronsted acids which can be suitably used are, for example, sulfuric, phosphoric, polyphosphoric, perchloric, chlorosulfonic, fluorosulfonic, alkyl and arylsuflonic (ethane, p-toluene) and related aromatic sulfonic acids, as well as chloroacetic and trifluoroacetic acids. The acidic oxides and sulfides useful as catalysts include a great variety of solid oxides and sulfides. Of particular usefulness are aluminum, silica and mixtures of aluminum and silica, although catalysts other than silica-aluminum compositions such as BeO, $Cr_2O_3$, $P_2O_5$, $TiO_2$, $ThO_2$, $Al_2(SO_4)_3$, $Al_2O_3 \cdot x\ Cr_2O_3$, $Al_2O_3 \cdot$ $Fe_2O_3$, $Al_2O_3 \cdot CoO$, $Al_2O_3$, MnO, $Al_2O_3 \cdot Vl_2O_3$, $Cr_2O_3 \cdot Fe_2O_3$, $MoS_2$ or $MoS_3$ may be also used. In addition, cation exchange resins which are solid acids are useful as catalyst, as well as methathetic cation forming agents such as anhydrous silver salts ($AgClO_4$, $AgBF_4$, $AgSbF_6$, $AgPF_6$, $AgAsF_6$ and $Ag_3PO_4$).

Although the concentration of Friedel Crafts catalyst is not critical, it is preferred to employ from 1.1 to 2.0 moles of catalyst to one mole of ketone and preferably 1.4 to 1.8 moles per mole of ketone. The reaction is suitably carried out in a solvent which is normally used for the Friedel Crafts reaction. Accordingly, such organic solvents as $CS_2$, fluorobenzene, polyhalogenated aromatic hydrocarbon, nitrobenzene, aliphatic hydrocarbon, halogenated aliphatic hydrocarbons and nitroalkanes. The reaction is carried out at a temperature of from about 0°C to about 150°C and preferably 20 to 100°C for a period of time sufficient to substantially complete the reaction.

The ketone starting material is readily prepared by condensing an appropriate acid halide of the formula:

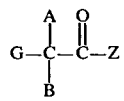

wherein A, B and G are as previously described and Z is halo, with fluorobenzene under Friedel Crafts conditions as described previously. Further, if desired, the acid halide may be condensed with the fluorobenzene to form the ketone and in situ go directly to the 5-fluoro-2-methyl-1-indanone. In the event that this procedure is desired additional Friedel Crafts catalyst is employed sufficient to carry out the two steps.

The following examples are given by way of illustration.

EXAMPLE 1

4'-Fluoro-3-hydroxy-2-methylpropiophenone

A mixture of 45.7 g. (0.3 moles) of 4'-fluoropropiophenone, 9 g. (0.3 moles) of paraformaldehyde, 4 g. (0.03 mole) of anhydrous potassium carbonate and 200 ml. of methyl alcohol is stirred at 35°C for two days. The reaction is quenched in water and acidified with hydrochloric acid. The product is extracted into benzene. The benzene layer is washed with water and concentrated in vacuo to give 4'-fluoro-3-hydroxy-2-methylpropiophenone.

EXAMPLE 2

5-Fluoro-2-methyl-1-indanone from 4'-fluoro-3-hydroxy-2-methylpropiophenone

A mixture of 18.2 g. (0.10 mole) of 4'-fluoro-3-hydroxy-2-methylpropiophenone and 12 g. of phosphorous pentoxide in 100 ml. of xylene is refluxed for one hour. The reaction is cooled, water is added and the xylene layer is washed with aqueous sodium hydroxide and water. The organic layer is then concentrated in vacuo to give 5-fluoro-2-methyl-1-indanone.

EXAMPLE 3

2-Bromo-4'-fluoro-2-methylpropiophenone

A slurry of 14 g. (0.105 mole) of anhydrous aluminum chloride in 14.4 g. (0.150 mole) of fluorobenzene and 24 ml. of carbon disulfide is cooled to 15°C. To it is added 23.8 g. (0.100 mole) of α-bromoisobutyryl bromide over 10–15 minutes at 15°–20°C. The reaction is stirred for five minutes at 20°C and then quenched on ice. The product is extracted into chloroform. The chloroform layer is washed with aqueous sodium bicarbonate, dried over anhydrous sodium sulfate and concentrated to give 2-bromo-4'-fluoro-2-methylpropiophenone.

EXAMPLE 4

5-Fluoro-2-methyl-1-indanone from 2-bromo-4'-fluoro-2-methylpropiophenone

To a slurry of 120.2 g. (0.90 mole) of anhydrous aluminum chloride in 54 ml. of carbon disulfide is added 122.6 g. (0.50 mole) of 2-bromo-4'-fluoro-2-methylpropiophenone at 15°–20°C over one hour. The mixture is warmed to 50°C over one hour, stirred at 50°C for three hours and quenched in ice. The product is extracted into toluene. The toluene layer is washed with aqueous sodium hydroxide and water and concentrated in vacuo to give 5-fluoro-2-methyl-1-indanone.

EXAMPLE 5

4'-Fluoro-2-methylacrylophenone

A slurry of 29.4 g. (0.220 mole) of anhydrous aluminum chloride in 38.4 g. (0.40 mole) of fluorobenzene under nitrogen is cooled to 15°C. Methylacryl chloride (21.9 g., 0.200 mole) is then added dropwise over 30 minutes while holding the temperature at 15°–20°C. The mixture is warmed to 30°C over 10 minutes, stirred at 30°C for 10 minutes and quenched in ice. The product is extracted into hexane. The hexane layer is dried over anhydrous sodium sulfate and concentrated in vacuo to give 4'-fluoro-2-methylacrylophenone.

EXAMPLE 6

5-Fluoro-2-methyl-1-indanone from 4'-fluoro-2-methylacrylophenone

Fifty grams (0.30 moles) of 4'-fluoro-2-methylacrylophenone is added to a slurry of 60.1 g. (0.45 moles) of anhydrous aluminum chloride in 27 ml. of carbon disulfide at 20°–25°C over one hour. The mixture is heated to 45°C over one hour and stirred at 45°C for one hour. The reaction is quenched in ice. The oily aqueous layer is extracted with toluene. The toluene layer is washed with aqueous sodium hydroxide and water and concentrated in vacuo to give 5-fluoro-2-methyl-1-indanone.

EXAMPLE 7

3-Chloro-4'-fluoro-2-methylpropiophenone

To a slurry of 22.7 g. (0.17 mole) of anhydrous aluminum chloride and 9.6 g. (0.10 mole) of fluorobenzene is added 14.1 g. (0.10 mole) of β-chloroisobutyrylchloride over 30 minutes at 20°–25°C. The mixture is aged for 30 minutes at 20°–25°C and then quenched in ice. The product is extracted into hexane. The hexane layer is dried over anhydrous sodium sulfate and concentrated in vacuo to give 3-chloro-4'-fluoro-2-methylpropiophenone.

EXAMPLE 8

5-Fluoro-2-methyl-1-indanone from 3-chloro-4'-fluoro-2-methylpropiophenone

Ten grams (0.05 mole) of 3-chloro-4'-fluoro-2-methylpropiophenone is added to 20 ml. of concentrated sulfuric acid at 20°–25°C and the mixture is warmed to 50°C. After stirring for three hours at 50°C, the reaction is quenched in ice. The product is extracted into hexane. The hexane layer is concentrated in vacuo to give 5-fluoro-2-methyl-1-indanone.

EXAMPLE 9

3-Dimethylamino-4'-fluoro-2-methylpropiophenone

A mixture of 15.2 g. (0.10 mole) of 4'-fluoropropiophenone, 8.2 g. (0.10 mole) of dimethylamine hydrochloride, 3.6 g. (0.12 mole) of paraformaldehyde in 20 ml. of absolute alcohol was stirred at 95°–100°C for three hours. The mixture is cooled and the precipitated product is filtered. The product is dissolved in water, made alkaline with sodium hydroxide. The free base is extracted into ether. The ether layer is dried over anhydrous sodium sulfate and concentrated in vacuo to give 3-dimethylamino-4'-fluoro-2methylpropiophenone

EXAMPLE 10

5-Fluoro-2-methyl-1-indanone from 3-dimethylamino-4'-fluoro-2-methylpropiophenone A mixture of 42 g. (0.20 mole) of 3-dimethylamino-4'-fluoro-2-methylpropiophenone and 100 ml. of concentrated sulfuric acid is warmed to 90°C over one hour and stirred at 90°C for two hours. The reaction is cooled and quenched in ice and the product extracted into toluene. The toluene layer is washed with aqueous sodium hydroxide and water and concentrated in vacuo to give 5-fluoro-2-methyl-1-indanone.

EXAMPLE 11

5-Fluoro-2-methyl-1-indanone from fluorobenzene and α-bromoisobutyryl bromide

To a slurry of 120.2 g. (0.90 mole) of anhydrous aluminum chloride in 54 ml. of carbon disulfide and 51.4 g. (0.535 mole) of fluorobenzene under nitrogen is added 115 g. (0.50 mole) of α-bromoisobutyryl bromide. The addition is accomplished at 15°–20°C over 75 minutes. The reaction is warmed to 50°C over 75 minutes, stirred at 50°C for 3 ½ hours and then quenched in ice. Toluene is added to extract the product. The toluene layer is washed with aqueous sodium hydroxide and water and concentrated in vacuo to give 79 g. (96%) of 5-fluoro-2-methyl-1-indanone.

EXAMPLE 12

5-Fluoro-2-methyl-1-(p-methylthiobenzyl)-indene

Twenty-five grams (1.04 moles) of magnesium turnings were placed in a dried flask under $N_2$ with 400 ml. of ether. Ten ml. of 0.05 molar p-methylthiobenzyl magnesium chloride in ether is added and the mixture is warmed to 30°C. About 2-3% of 39.7 g. (0.23 moles) of p-methylthiobenzyl chloride in 75 ml. of toluene is added. After 3–5 minutes of stirring an exotherm to 32°–33°C occurs signifying initiation of the reaction. After aging for 5 minutes, the rest of the benzyl chloride is added dropwise over 90 minutes. The reaction is aged for 30 minutes with stirring. 5-Fluoro-2-methyl-1-indanone (32.6 g., 0.199 mole) is added dropwise over 45 minutes. After aging for 30 minutes, the milky supernatant mixture is decanted from the magnesium. The flask and residual magnesium are rinsed with toluene. The reaction is then quenched by the addition of 120 ml. of 3N sulfuric acid. The lower layer is discarded. To the organic layer is added 80 ml. of 1:10 concentrated sulfuric acid, acetic acid and the two-phase mixture, stirred vigorously for one hour and water (100 ml.) is added. The bottom layer is discarded and the organic layer is washed with 100 ml. of water and 200 ml. of 2N sodium hydroxide. After a final water wash the organic layer is concentrated to give 5-fluoro-2-methyl-1-(p-methylthiobenzyl)-indene.

Similarly, when p-methylsulfinylbenzyl chloride is used in place of p-methylthiobenzyl chloride in the above example, the corresponding p-methylsulfinylbenzyl indene is obtained.

EXAMPLE 13 p-Methylthiobenzyltriphenylphosphonium chloride 17.3 of p-methylthiobenzyl chloride is added to 28 g. of triphenylphosphine in 80 ml. of benzene. The reaction was heated for 4 hours, then cooled and the product, p-methylthiobenzyltriphenylphosphonium chloride, was collected by filtration. There is obtained 19 g., melting point 257°–258°C.

In a similar manner, when p-methylsulfinylbenzyl chloride is used, the product is p-methylsulfinylbenzyltriphenylphosphonium chloride, melting point 258°–262°C with gasing.

EXAMPLE 14

5-Fluoro-2-methyl-1-(p-methylthiobenzyl)-indene

A.

5-Fluoro-2-methyl-1-(p-methylthiobenzylidene)-indane

169 Mg. (1.5 mm) of potassium t-butoxide is dissolved in 2 ml. of DMSO and treated with 651 mg. (1.5 mm) of p-methylthiobenzyltriphenylphosphonium chloride dissolved in 1 ml. of DMSO. To this solution is added 270 mg. (1.65 mm) of 5-fluoro-2-methyl-1-indanone in 2 ml. of DMSO. The solution is heated at 75°C for 15.5 hours. Benzene and water are added and the benzene layer is washed five times with water. The benzene layer is dried over $Na_2SO_4$ and evaporated to dryness under vacuum. The weight is 915.6 mg. This material is eluted through 8 g. of silica gel with benzene to remove triphenylphosphine oxide. The eluate weights 372 mg. after removal of solvent. This is rechromatographed through 15 g. of silica gel using hexane and 95.9 mg. of 5-fluoro-2-methyl-1-(p-methylthiobenzylidene)-indane is isolated, melting point 67°–70°C.

B. 5-Fluoro-2-methyl-1-(p-methylthiobenzyl)-indene

50 Mg. of the benzylidene compound from A above is mixed with 1 ml. of acetic acid containing 100 mg. of sulfuric acid and the reaction mixture stirred for 1 hour at room temperature. The mixture is then diluted with water and extracted with ether. The ether extract is concentrated in vacuo to give the subject compound.

Similarly, when the p-methylsulfinylbenzyl triphenylphosphonium chloride is used, the corresponding p-methylsulfinylbenzyl indene compound is obtained.

EXAMPLE 15

5-Fluoro-2-methyl-1-(p-methylsulfinylbenzyl)-indene 500 mg. (1.755 mm) of 5-fluoro-2-methyl-1-(p-methylthiobenzyl)-indene is dissolved in 5 ml. of chloroform. To this solution is added 30% hydrogen peroxide (equivalent to 2.645 mm). The reaction mixture is aged for one hour at room temperature followed by the addition of 5 ml. of glacial acetic acid and aged for an additional hour. The reaction mixture is then diluted with 25 ml. of 1:1 benzene-ether and extracted with 6 × 25 ml. of 3% aqueous sodium chloride. The solution is then dried over sodium sulfate and evaporated in vacuo to yield an oil. Recrystallization from ice-cold isopropanol gives 5-fluoro-2-methyl-1-(p-methylsulfinylbenzyl)-indene.

EXAMPLE 16

5-Fluoro-2-methyl-1-(p-methylthiobenzyl)-indenylidene-3-acetic acid

To 41.8 g. (147 mmole) of the preceeding indene (from Example 12) is added 150 ml. of methanolic Triton B solution (53.2 g., dry basis; 317.5 mmole) and the batch, under a nitrogen atmosphere, is brought to 35°C. 14.63 G. glyoxylic acid (198 mmole) is added and the batch, which warms to 50°-55°C is aged one hour at 50°C. It is then diluted with 250 ml. of water and acidified with dilute sulfuric acid. The product obtained in 90% yield is recrystallized to give the pure subject product, melting point 185.5°–188°C.

When sodium hydroxide and tetramethylammonium chloride or tetramethylammonium hydroxide is used in place of Triton B in the above example, the indenylidene-3-acetic acid is obtained.

Similarly, when 5-fluoro-2-methyl-11-(p-methylsulfinylbenzyl)indene is used in place of the corresponding methylthio compound in the above example, there is obtained 5-fluoro-2-methyl-1-(p-methylsulfinylbenzyl)-indenylidene-3-acetic acid.

EXAMPLE 17

5-Fluoro-2-methyl-1-(p-methylthiobenzylidene)-indene-3-acetic acid

A suspension of 34.2 g. of 5-fluoro-2-methyl-1-(p-methylthiobenzyl)-indenylidene-3-acetic acid (from Example 16) in 342 ml. of glacial acetic acid and 137 ml. of concentrated HCl is stirred under a nitrogen atmosphere at 90°C for 10 hours. The reaction is cooled over 2 to 3 hours to room temperature and aged an additional 3 hours at 20°–25°C. The batch is filtered, washed with 70:30 acetic acid-water (ca. 100 ml.) then water-washed to remove excess acid. There is obtained 93% of product, melting point 180°–183°C.

Similarly when 5-fluoro-2-methyl-1-(p-methylsulfinylbenzyl)-indenylidene-3-acetic acid is used in the above example in place of the corresponding methylthio compound, there is obtained 5-fluoro-2-methyl-1-(p-methylsulfinylbenzylidene)-indene-3-acetic acid. The reaction may be conducted in an aprotic solvent such as 1,2-dichloroethane under 100 p.s.i.g. of HCl gas at 50°–100°C.

EXAMPLE 18

5-Fluoro-2-methyl-1-(p-methylsulfinylbenzylidene)-indene-3-acetic acid

Seventeen grams (50 mmole) of the product from Example 17 is stirred in 94 ml. of chloroform and 40 ml. of acetic acid under nitrogen and the temperature brought to 30°C. To this slurry is added 5.3 ml. of 9.6N aqueous $H_2O_2$ (51 mmole) over one minute. The temperature is brought to 35°C. The batch is aged a total of 6 hours, maintaining 35°C internal temperature. After the age period, 125 ml. of water is added and the $CHCL_3$ layer concenetrated to a small volume in vacuo. The residue is crystallized from 75 ml. of ethanol and the slurry cooled to 0°–5°C and aged at 0°–5°C. The product is filtered and washed with 15 ml. of cold (0°–5°C) 2BA ethanol and dried in vacuo at 80°C. The product weighs 16.3 g. (92%), melting point 183°–185°C.

Similarly, when sodium periodate or potassium hypochlorite is used in place of hydrogen peroxide in the above example, there is obtained the desired compound.

EXAMPLE 19

2-Dimethylaminomethyl-4'-fluoropropiophenone

A slurry of 14 g. (0.105 mole) of anhydrous aluminum chloride in 14.4 g. (0.150 mole) of fluorobenzene and 24 ml. of carbon disulfide is cooled to 15°C. To it is added 0.100 mole of α-(dimethylaminomethyl)propionyl bromide hydrobromide over 10–15 minutes at 15°–20°C. The reaction is stirred for five minutes at 20°C and then quenched on ice. The product is extracted into chloroform. The chloroform layer is washed with aqueous sodium bicarbonate, dried over anhydrous sodium sulfate and concentrated to give 2-bromo-4'-fluoro-2-methylpropiophenone.

EXAMPLE 20

5-Fluoro-2-methyl-1-(p-methylthiobenzyl)-indene 13.44 Grams (0.56 mole) of magnesium turnings are placed in a dried flask under $N_2$ with 125 ml. of ether and a crystal of iodine. Six ml. of 65 ml. solution of 24.2 g. (0.14 mole) of p-methylthiobenzyl chloride in ether is added. After 3 to 5 minutes of stirring the iodine color disappears and the reaction begins. After aging for 5 minutes, the rest of the benzyl chloride is added dropwise over 45 minutes. It is rinsed in with 10 ml. of ether and the reaction aged for 2 hours with stirring. 21 Grams (0.128 mole) of 5-fluoro-2-methyl-1-indanone dissolved in 50 ml. of ether is added dropwise over 30 minutes. After aging for 1 hour, the milky supernatent mixture is decanted from the magnesium into 100 ml. of acetic acid. The flask and residual magnesium are rinsed into the acid solution with 4 × 50 ml. of benzene. Two hundred ml. of water are added, the layers are separated and the organic layer is washed with 5 × 200 ml. water. It is stripped to dryness after drying over $Na_2SO_4$. The crude reaction product is crystallized from hexane to give pure 5-fluoro-2-methyl-1-(p-methylthiobenzyl)-indene, melting point 58°–59°C.

EXAMPLE 21

5-Fluoro-2-methyl-1-(p-methylthiobenzylidene)-indene-3-acetic acid

A suspension of 34 grams of 5-fluoro-2-methyl-1-(p-methylthiobenzyl)-indenylidene-3-acetic acid in 150 ml. of ethylene dichloride is heated to 70°C in a glass lined autoclave. Anhydrous hydrogen chloride is admitted unitl the pressure reaches 95 pounds. The reaction is stirred under these conditions for 10 hours and the excess gas is then vented. The product slurried is cooled to 0-5°C and after one hour is filtered and washed with fresh ethylene dichloride. The yield product is 80%.

What is claimed is:

1. A cis and trans compound of the formula:

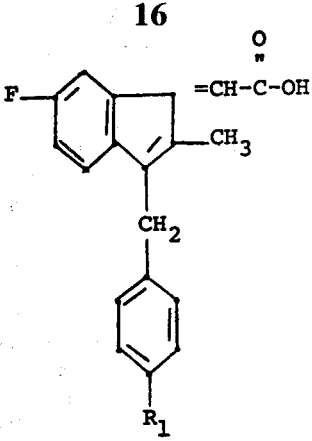

wherein
$R_1$ is methylthio or methylsulfinyl.